United States Patent [19]

Sykes et al.

[11] 4,205,068
[45] May 27, 1980

[54] β-LACTAMASE INHIBITOR EM4615

[75] Inventors: Richard B. Sykes, Rocky Hill; J. Scott Wells, Ringoes; Pacifico A. Principe, South River; Wen C. Liu, Princeton Junction, all of N.J.

[73] Assignee: E. R. Squibb & Sons, Inc., Princeton, N.J.

[21] Appl. No.: 906,906

[22] Filed: May 18, 1978

[51] Int. Cl.$^2$ .............................................. A61K 37/64
[52] U.S. Cl. .................................. 424/117; 435/170; 435/184; 435/868; 435/867
[58] Field of Search ............................ 195/96, 80, 65; 424/115, 117; 435/170, 184

[56] References Cited
U.S. PATENT DOCUMENTS
4,078,056  3/1978  Weinstein et al. .................. 424/117

FOREIGN PATENT DOCUMENTS
1363075  8/1974  United Kingdom .

OTHER PUBLICATIONS

Journal of Antibiotics, (Japan), vol. 27, pp. 493–501, (1974).
Journal of Antibiotics, (Japan), vol. 25, pp. 473–474, (1972).
Journal of Antibiotics, (Japan), vol. 26, pp. 51–54, (1973).

Primary Examiner—Lionel M. Shapiro
Attorney, Agent, or Firm—Lawrence S. Levinson; Donald J. Barrack

[57] ABSTRACT

A substance which inhibits the enzyme β-lactamase, produced by a wide range of microorganisms, is obtained when species of the microorganism Micromonospora are cultivated under aerobic fermentation conditions and this inhibitor can be isolated from the fermentation medium by extraction. This substance, denominated EM4615, is useful to enhance the effectiveness of β-lactam antibiotics such as penicillins and cephalosporins.

10 Claims, 1 Drawing Figure

INFRARED SPECTRUM OF EM 4615 (Sodium Salt) IN KBr

β-LACTAMASE INHIBITOR EM4615

BACKGROUND AND BRIEF SUMMARY OF THE INVENTION

The β-lactamases are enzymes produced by many pathogenic microorganisms such as bacteria of the genera Staphylococcus, Escherichia, Klebsiella, Proteus, Pseudomonas, Enterobacter, etc. They have the capacity to open the β-lactam ring of antibacterial agents with this structural feature, notably the penicillins and cephalosporins. This reaction inactivates the effectiveness of the antibacterial agent in combatting infection caused by the bacteria which in turn gives rise to resistance by strains of the disease-causing microorganism to treatment with the antibacterial agent. A β-lactamase inhibitor can therefore be useful in protecting the antibacterial agent against degradation by the enzyme and thus enhance the effectiveness of the antibacterial agent.

Cultures from Actinomycetes have been reported as producing β-lactamase inhibiting substances. See British Pat. No. 1,363,075; J. Antibiotics 25, 473 (1972), 26, 51 (1973).

Species of Micromonospora have been described which produce antibiotics such as gentamicin, sisomycin, neomycin and others. See, for example, J. Antibiotics 27, 493 (1974); U.S. Pat. No. 4,078,056, Mar. 7, 1978. These Micromonospora produced antibiotics have typical spectra of antibacterial activity against various microorganisms such as *Streptococcus fecalis, Staphylococcus aureus, Escherichia coli, Candida albicans,* etc., but the production of β-lactamase inhibitors by this genus has not been reported.

We have now found that species of the microorganism Micromonospora can be made to produce the substance EM4615 which inhibits the effect of β-lactamase enzymes. EM4615 is produced by culturing species of the microorganism Micromonospora at about 20° to 35° C., preferably about 25° under submerged aerobic conditions in an aqueous nutrient medium containing an assimilable carbohydrate and nitrogen source for about 48 to 240 hours, preferably about 144 hours. The β-lactamase inhibitor EM4615 can then be extracted from the fermentation broth. It is isolated by centrifuging the completed broth to remove the mycelium and other solids, extracting the remaining broth with a lower alkanol, preferably n-butanol, at a low pH, e.g., approximately pH 2, then back extracting the alcohol extract with water at about pH 7 to 9. The water extract contains the β-lactamase inhibitor.

This invention therefore relates to the β-lactamase inhibitor EM4615 and to a method for producing it.

FIG. 1 shows the infrared spectrum of the sodium salt of EM4615 in KBr.

DETAILED DESCRIPTION OF THE INVENTION

Figure 1:
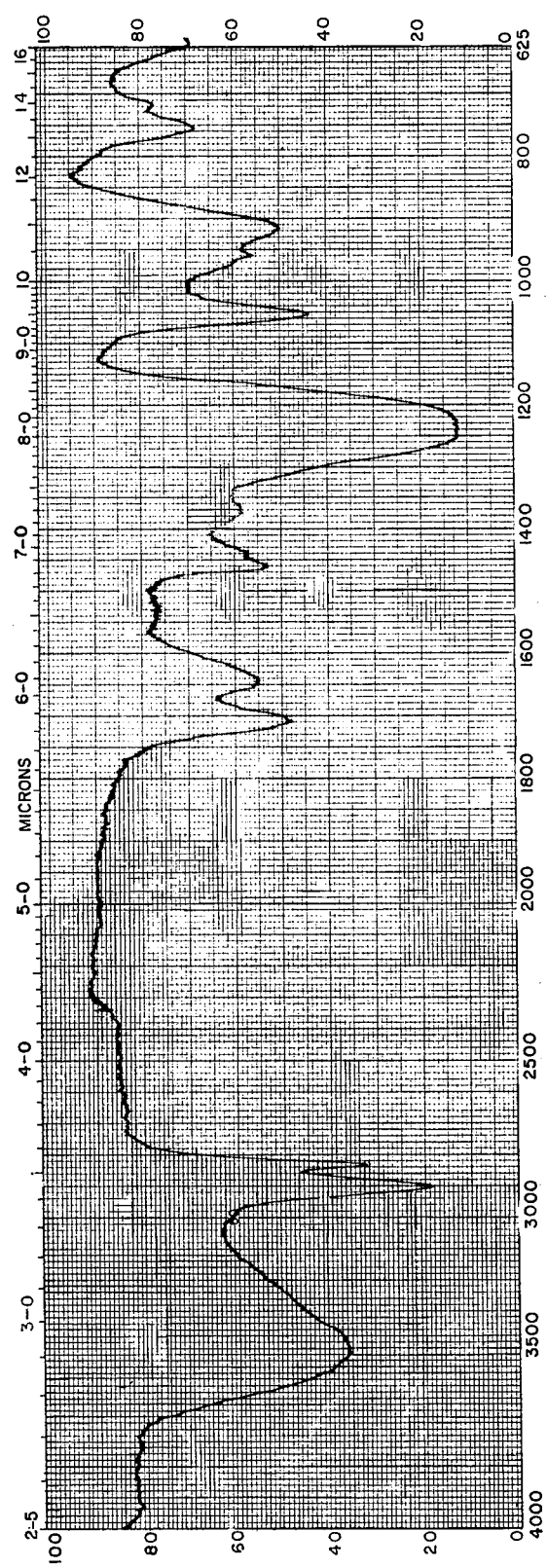

The β-lactamase inhibitor of this invention is produced by species of the microorganism Micromonospora. The preferred microorganism has been isolated from a soil sample and designated Micromonospora sp. SC11,133 which is a strain of *Micromonospora chalcea*. A subculture of this species has been deposited in the collection of the American Type Culture Collection, Rockville, Maryland and can be obtained under the accession number ATCC 31395. Other β-lactamase inhibitor producing strains of Micromonospora can also be obtained from the same repository, e.g., *Micromonospora chalcea* ATCC 21561; *Micromonospora carbonacea* ATCC 27114, *Micromonospora carbonacea* ATCC 27115.

The Microorganism

The preferred microorganism useful for the preparation of EM4615 is a species of Micromonospora hereinafter designated *Micromonospora chalcea* sp. SC 11,133. For isolating and characterizing the organism, a portion of the air dried soil sample is stamped on a nutrient agar containing:

|  | Grams |
| --- | --- |
| Soluble starch | 10 |
| Casein (vitamin free) | 0.3 |
| $KNO_3$ | 2.0 |
| NaCl | 2.0 |
| $K_2HPO_4$ | 2.0 |
| $MgSO_4 . 7H_2O$ | 0.05 |
| $CaCO_3$ | 0.02 |
| $FeSO_2 . 7H_2O$ | 0.01 |
| Agar | 20 |
| Distilled water to 1000 ml. | |

The medium is adjusted to pH 7.0 and sterilized in an autoclave at 121° C. for 20 minutes. After 7 to 10 days incubation at 25° C. colonies of the *Micromonospora chalcea* sp. SC 11,133 are isolated from the plated soil. These isolated colonies are then grown on a medium containing:

|  | Grams |
| --- | --- |
| Beef extract | 1.0 |
| Yeast extract | 1.0 |
| NZ amine A | 2.0 |
| Glucose | 10.0 |
| Agar | 15.0 |
| Distilled water to 1000 ml. | |

The medium is adjusted to pH 7.3 and autoclaved at 121° C. for 30 minutes.

The organism producing EM4615 forms no true aerial mycelium. Spores are borne singly at the ends of simple sporophores appearing in monopodially arranged clusters.

Hydrolysates of purified cell walls contain meso-DAP, glycine, xylose and arabinose. This organism is assigned to the genus Micromonospora based upon its characteristic morphology and the type II cell wall.

Culture characteristics are based on observations made at 14 and 21 days on Micromonospora maintenance agar. Plates are incubated at 28° C. The color of the vegetative mycelium at 14 days is moderate organge (ISCC No. 53) matching color chip (4 lc) in the Color Harmony Manual. At 21 days the vegetative mycelium is overlayed by a dry black mass of spores. The colony reverse is the same as the surface at 14 days becoming darker after sporulation occurs. No soluble pigment is produced. The color of the mycelium is the same on tomato paste oatmeal agar and on yeast extract-dextrose agar.

*Micromonospora chalcea* sp. SC 11,133 produces a β-lactamase inhibitor which inhibits the action of β-lactamases especially from gram negative organisms.

The culture grows optimally between 30° and 37° C. with no growth above 45° C. It grows on buffered media between pH 6.0 and 8.0 with no growth at pH 5.5. It is proteolytic as evidenced by positive clearing on milk and gelatin plates. Starch is hydrolyzed. No growth occurs on media containing more than 1.5% NaCl.

The following carbohydrates can be utilized as a sole carbon source: glucose, d-xylose, l-arabinose, fructose, raffinose, melibiose, sucrose and lactose. No growth or poor growth is obtained on glycerol, mannitol, inositol and rhamnose.

To form the β-lactamase inhibitor, *Micromonospora chalcea* sp. SC 11,133 is grown at 25° C. under submerged aerobic conditions in an aqueous nutrient medium containing an assimilable carbohydrate and nitrogen source. The fermentation is carried out for approximately 48 to 240 hours, preferably about 144 hours, at the end of which time the β-lactamase inhibitor has been formed.

After fermentation has been completed the broth in centrifuged to remove the mycelium. The β-lactamase inhibitor is extracted from the supernatant with butanol at pH 2.0 and back extracted into water to pH 9.0. The aqueous material is freeze dried. Further purification is effected by column chromatography on Sephadex LH20 (polydextrane anion exchange resin) eluting with methanol:water (9:1). The active fraction is then rechromatographed on Sephadex G15 ion exchange resin. The active fractions are lyophilized.

EM4615 is a strong acid and is moderately acid labile. It is preferably used as the salt of whatever cation may be suitable for the purpose at hand. Salts of divalent metals, e.g., magnesium, calcium, barium, zinc, etc., have low solubility in water and can be obtained by adding an aqueous solution of the halide, preferably chloride, of such metals, to an aqueous solution of a soluble EM4615 salt, e.g., ammonium salt or alkali metal salt such as sodium, potassium salts, etc. Soluble salts of EM4615 can be interconverted by distribution in butanol and a concentrated aqueous solution of the sulfate of the desired cation. The salt of EM4615 is extracted into butanol under these conditions.

The substance EM4615 is an inhibitor of the enzyme β-lactamase. It is specific to β-lactamases, and does not inhibit other unrelated enzymes such as alcohol dehydrogenase, carboxypeptidases and angiotensin converting enzyme at or below 100 µg/ml. It therefore can be used to protect substances which are inactivated by β-lactamases from degradation by these enzymes and to enhance the antibacterial activity of β-lactamase affected antibiotics. It is especially valuable for increasing the antibacterial activity of penicillins and cephalosporins against resistant organisms.

The β-lactamase inhibitor EM4615 or salt thereof can be used as the sole therapeutic agent in a composition which is administered at the same time or in conjunction with antibiotic therapy or it may be present together with other therapeutic agents in a fixed combination. EM4615 is useful as a β-lactamase inhibitor at dosage levels of about 5 mg. to 150 mg/kg/day preferably about 10 to 100 mg/kg., in the treatment of bacterial infections due to gram positive and gram negative organisms which are conventionally treated with antibiotics such as those named below, e.g., infections of the respiratory tract, urinary tract, etc., in various mammalian species. It can be used in the treatment of various bacterial infections of domestic animals such as mastitis in cattle. The substance EM4615 can be administered by the oral route, which is preferred, or intramuscularly, intravenously, intraperitoneally or subcutaneously. The substance or a physiologically acceptable salt thereof can be formulated in tablets, capsules, elixirs or the like for oral administration. Sterile solutions or suspensions can be used for parenteral use.

About 50 to 500 mg. of EM4615 or salt thereof can be compounded with a physiologically acceptable vehicle, carrier, excipient, binder, preservative, stabilizer, flavor, etc., in a conventional dosage form according to accepted pharmaceutical practice. The amount of active substance is selected so as to provide a dosage in the range indicated.

β-lactam antibiotics susceptible to β-lactamases which can be included in compositions containing also the β-lactamase inhibitor EM4615 or salt thereof are for example, penicillins and cephalosporins such as benzylpenicillin, ampicillin, epicillin, hetacillin, phenoxymethylpenicillin, carbenicillin, methicillin, amoxicillin, propicillin, ticarcillin, cyclacillin, cephalexin, cephaloridine, cefoxitin, cefazolin, cefamandole, cefadroxil, cephapirin, cephalothin, cefazolin, cephradine, cephaloglycin, salts or esters thereof, and other well known antibiotics of this type.

The antibiotics of the type named above are usually formulated in compositions such as those described above in amounts of about 50 to 1000 mg. The β-lactamase inhibitor can be included so that the ratio of antibiotic to β-lactamase inhibitor is about 1:20 to 15:1, preferably about 1:3 to 3:1. The total daily dosage of such compositions are generally the usual daily amount of the antibiotic selected, conventionally in the range of about 500 to 3000 mg/day in single or divided daily doses.

The following examples are illustrative of the invention. Temperatures are on the Celsius scale.

EXAMPLE 1

*Micromonospora chalcea* sp. SC 11,133 (ATCC 31395) is maintained on the following sterilized agar medium (A):

|  | Grams |
| --- | --- |
| Beef extract | 3 |
| Tryptone | 5 |
| Yeast Extract | 5 |
| Soluble starch | 24 |
| Dextrose | 1 |
| Agar | 15 |
| $CaCO_3$ | 4 |
| Tap water to 1 liter | |

A loopful of surface growth from an agar slant (Medium A) of *Micromonospora chalcea* sp. (SC 11,133) is used to inoculate each of six 500 ml. Erlenmeyer flasks, each containing 100 ml. of the following sterilized medium (B):

|  | Grams |
| --- | --- |
| Nutrisoy flour | 15 |
| Soluble starch | 15 |
| Glucose | 50 |
| $CoCl_2 . 6H_2O$ | 0.005 |
| $CaCO_3$ | 10 |
| Distilled water to 1 liter | |

The flasks are then incubated at 28° C. on a rotary shaker (280 rpm; 2 inch stroke) for approximately 96 hours. After the appropriate incubation, as described above, 5% (vol/vol) transfers are made from the grown culture flasks to one hundred 500 ml. Erlenmeyer flasks each containing 100 ml. of the following sterilized medium (C):

|  | Grams |
|---|---|
| Yeast extract | 4 |
| Malt extract | 10 |
| Dextrose | 4 |
| $FeSO_4 \cdot 7H_2O$ | 0.3 |
| Distilled water to 1 liter | |
| pH adjusted to 7.0 before sterilization | |

After inoculation the flasks are incubated at 25° C. on a rotary shaker (300 rpm; 2 inch stroke) for approximately 144 hours. At this time the contents of the flasks are pooled and the broth is centrifuged yielding approximately 9 liters of supernatant broth.

The $\beta$-lactamase inhibitory activity is detected microbiologically using *Micrococcus luteus* and benzyl penicillin.

EXAMPLE 2

A 250 liter batch of *Micromonospora chalcea* sp. SC11,133 is fermented in a 100 gal. stainless steel vessel with the media and operating conditions described below.

Stage 1

Inoculum: Culture of *Micromonospora chalcea* sp. SC 11,113 preserved by lyophilization in milk and grown out on the following sterilized medium (A):

| Beef extract | 3 |
|---|---|
| Tryptone | 5 |
| Yeast Extract | 5 |
| Soluble starch | 24 |
| Dextrose | 1 |
| Agar | 15 |
| $CaCO_3$ | 4 |
| Tap water to 1 liter | |

A loopful of surface growth from the agar slant (medium A) of *Micromonospora chalcea* sp. (SC 11,133) is used to inoculate each of three 500 ml. Erlenmeyer flasks, each containing 100 ml. of the following sterilized medium (B):

|  | Grams |
|---|---|
| Nutrisoy flour | 15 |
| Soluble flour | 15 |
| Glucose | 50 |
| $CoCl_2 \cdot 6H_2O$ | 0.005 |
| $CaCO_3$ | 10 |
| Distilled water to 1 liter | |

The flasks are then incubated at 28° on a rotary shaker (280 rpm; 2 inch stroke) for approximately 96 hours. After the appropriate incubation, as described above, 5% (vol/vol) transfers are made from the grown culture flasks to 3 four liter Erlenmeyer flasks, each containing 800 ml. of the same sterilized medium (B) described above. The flasks are once again incubated at 28° C. on a rotary shaker (280 rpm; 2 inch stroke) for approximately 72 hours.

Stage 2

Inoculum: 1,500 ml. from the first stage.
Medium (B) as described above

Thirty liters of medium (B) containing the inoculum is incubated for 72 hours at 28° C. in a 10 gallon stainless steel vessel. During incubation, the broth is aerated at the rate of 2.3 cubic feet per minute with agitation at 220 rpm.

Stage 3

Inoculum: 12,500 ml. from stage 2
Medium (C):

|  | Grams |
|---|---|
| Yeast extract | 4 |
| Malt extract | 10 |
| Dextrose | 4 |
| $FeSO_4 \cdot 7H_2O$ | 0.3 |
| Distilled water to 1 liter | |
| pH adjusted to 7.0 before sterilization. | |

250 liters of medium (C) containing the inoculum is incubated for 144 hours at 25° C. in a 100 gallon stainless steel vessel. During incubation, the broth is agitated at 155 rpm. and aerated at the rate of 10 cubic feet per minute.

EXAMPLE 3

The mycelium is removed by centrifugation to give (185) liters of supernatant.

EXAMPLE 4

The filtrate obtained in Example 3, is adjusted to pH 2 with 3 N HCl and quickly extracted with 80 liters of n-butanol. The butanol layer is extracted with 40 liters of pH 7 water as soon as possible. In general, the active material stays in butanol at pH 2 not more than 10 minutes to avoid losing the activity of the $\beta$-lactamase inhibitor. Once the activity is extracted into water at pH 7.0 the danger of losing activity is much less. The pH 7 water extract is concentrated and freeze dried. From 185 liters of broth filtrate, approximately 300 g. of freeze dried solid is obtained which represents roughly one third of the original activity in the filtrate; the spent aqueous supernatant and the spent butanol does not have a substantial amount of activity.

EXAMPLE 5

A sample of 50 g. of the freeze-dried solid from Example 4, is dissolved in 400 ml. of water. This water solution is slowly poured into a large flask containing 4 liters of methanol with stirring. After the precipitation is complete, the mixture is stirred for 15 more minutes and then centrifuged. The precipitate has some activity, but most of the activity goes into the methanol. The clear methanol supernatant is concentrated under reduced pressure to about 600 ml. The active compound starts to precipitate out. The mixture is allowed to stand at 5° overnight and is then centrifuged. The precipitate is worked up with acetone and vacuum dried, giving 8.5 g. of dry powder.

EXAMPLE 6

One gram of the dry powder from Example 5 is dissolved in 10 ml. of water and chromatographed on a G-15 Sephadex (bead formed dextran gel) column (4×73 cm) packed in water. The column is eluted with water and 15 ml. fractions are collected. Fractions are spotted on cellulose plates (made by Schleicher & Schuell, Keene, N.H.), developed with acetonitrile/water (5:1) system and sprayed with RP1 enzyme and chromogenic cephalosporin. The active fractions are pooled according to the results of TLC analysis and freeze dried. Two components are separated on the G-15 Sephadex column. The main component with over 90% of the bioactivity and dry weight is the sodium salt and has an $R_f$ value of about 0.6 (A), and the minor component which is only weakly active, has an $R_f$ value of about 0.4 (B).

EXAMPLE 7

A sample of 0.5 g. of the dry powder from Example 5 is dissolved in 200 ml. of methanol. The solution is concentrated to about 40 ml. without precipitation, and then is chromatographed on an LH20 Sephadex (hydroxypropylated form of bead formed dextran gel) column (3×60 cm) packed in methanol. Elution of the column is carried out with methanol and 15 ml. fractions are collected. The fractions are assayed as described in Example 6 and the active fractions are combined and concentrated to dryness under reduced pressure and below 30°. There is no separation of the components on the LH20 Sephadex column although there is considerable purification of the active compound.

TLC is used to separate and hence distinguish EM4615 from the reported β-lactamase inhibitors, notably MM4550 and clavulanic acid. When chromatographed on cellulose plates (S & S) and developed with acetonitrile-water (6-1), the $R_f$ values of the various β-lactamase inhibitors are as follows:

|  | $R_f$ |
|---|---|
| EM4615 (A) | 0.57 |
| Clavulanic Acid (Li salt) | 0.49 |
| EM4615 (B) | 0.42 |
| MM4550 | 0.29 |

EXAMPLE 8

Purified EM4615, either from Example 6 or 7 are transformed to the barium salt and purified further.

A methanol solution of Ba(OH)$_2$ is added to a methanol solution of EM4615 dropwise with stirring. The addition of Ba(OH)$_2$ is continued until the precipitation is complete. Then the mixture is centrifuged. The precipitate is washed with water thoroughly to remove Ba(OH)$_2$ and any other water soluble impurities. It is then washed with methanol thoroughly and vacuum dried.

EXAMPLE 9

Properties of EM4615:

1. M.P.—Na salt—No definite M.P. (decomposes). Ba salt—144°–146° C. (d).
2. U.V. λmax 214, $E_1^{1\%}$ 95 (water)
3. I.R.—The spectrum for the Na salt and the Ba salt are nearly identical. Each has a carbonyl peak of 5.85μ and 5.90μ, respectively; each has a peak for sulfate at about 8.0μ. The I.R. spectrum for the Na salt is shown in FIG. 1.
4. TLC—When chromatographed on cellulose (S & S) plate, developed with acetonitrile-water (5:1), and detected by spraying with RP1 enzyme [Class III β-lactamase enzyme from *E. coli* (Richmond & Sykes, Recent Advances in Microbial Physiology, Vo. 9, 31–88, Ed. Rose & Tempest, Academic Press, 1973)], followed by chromogenic cephalosporin [O'Callaghan et al., Antimicrobial Agents and Chemotherapy 4, 283–288 (1972)], the $R_f$ values are about 0.6 for the Na salt and about 0.4 for the Ba salt.
5. Solubility—Na salt—soluble in water, MeOH; insoluble in acetone, CHCl$_3$. Ba salt—insoluble in water, MeOH, acetone, CHCl$_3$; soluble in dimethylsulfoxide and dimethylformamide.
6. Elemental analysis: Na salt—C, 49.99%; H, 7.71%; O, 23.69%; S, 10.51%; Na, 8.10%.
7. Approximate empirical formula (based on above) $C_{12.7} H_{23.3} S_{(1)} O_{4.52} Na_{1.07}$.
8. Paper electrophoresis of either the sodium or barium salt of Em4615, carried out in Werum buffers, [J. Chromatog. 3, 125 (1960)] pHs 3.3, 4.7, 7.2, 8.0 and 9.3, containing 30% formamide, reveal the presence of a single, strongly acidic component with β-lactamase inhibitory activity.

The specific revelation of this substance on electropherograms, dried for 1 hour at 110° C., may be accomplished by use of the following reagents:

(1) TEM or RP1 enzyme, followed by the chromogenic cephalosporin 87/312. Em4615 appears as yellow spot on a pink background.

(2) 0.1% methanolic solution of 6-ethoxy-1-methyl-2-(m-nitrostyryl)-quinoline methosulfate. Em4615 appears as an intensely yellow fluorescent spot when veiwed under 360 nm ultraviolet light.

(3) 0.2% methanolic solution of 2′,7′-dichlorofluorescein. EM4615 appears as a blue fluorescent spot against a yellow background when viewed under 360 nm ultraviolet light.

(4) 0.1% ethanolic solution of 1-anilinonaphthalene-8-sulphonate. EM4615 appears as bright blue fluorescent spot against a dark background when viewed under 360 nm ultraviolet light.

The electrophoretic mobility of EM4615, in Am-units (Werum, supra), is as follows:

| pH | Am-Value |
|---|---|
| 3.3 | −128 |
| 4.7 | −123 |
| 7.2 | −123 |
| 8.0 | −123 |
| 9.3 | −123 |

EXAMPLE 10

Enzyme inhibition studies carried out with several β-lactamase preparations using the inhibitor obtained in Example 7 give the following results:

| Enzyme Preparation | $I_{50}$ μg/ml | Substrate |
|---|---|---|
| *Staphylococcus aureus* (SC 10839) | 6 | Ampicillin |
| *Escherichia coli* (SC 10837) | 1 | Cephaloridine |
| *Escherichia coli* (SC 10979) | 0.1 | Cephaloridine |
| *Klebsiella aerogenes* (SC 10947) | 2 | Cephaloridine |
| *Enterobacter cloacae* (SC 10945) | 0.04 | Cephaloridine |

The following fermentation media have been found effective for the production of EM4615, and may be substituted for medium (C) above. The more productive media are listed first.

| Medium D | |
|---|---|
| | Grams |
| Oatmeal | 20 |
| Tomato Paste | 20 |
| $FeSO_4 \cdot 7H_2O$ | 1.0 |
| Distilled water to 1 liter | |
| pH adjusted to 7.0 before sterilization. | |

| Medium E | |
|---|---|
| | Grams |
| Nutrisoy flour | 10 |
| Glucose | 20 |
| $FeSO_4 \cdot 7H_2O$ | 0.1 |
| $MnSO_4 \cdot 4H_2O$ | 0.05 |
| $CoCl_2 \cdot 6H_2O$ | 0.001 |
| $MgSO_4 \cdot 7H_2O$ | 1.0 |
| $CaCO_3$ | 10 |
| Distilled water to 1 liter | |
| pH adjusted to 7.0 before sterilization. | |

| Medium F | |
|---|---|
| | Grams |
| Yeast extract | 4 |
| Malt extract | 10 |
| Glucose | 4 |
| $FeSO_4 \cdot 7H_2O$ | 0.1 |
| $MnSO_4 \cdot 4H_2O$ | 0.05 |
| $CoCl_2 \cdot 6H_2O$ | 0.001 |
| $MgSO_4 \cdot 7H_2O$ | 1.0 |
| $CHCO_3$ | 10 |
| Distilled water to 1 liter | |
| pH adjusted to 7.0 before sterilization. | |

| Medium G | |
|---|---|
| | Grams |
| Soluble starch | 20 |
| Glucose | 10 |
| Malt extract | 1 |
| Nutrisoy flour | 10 |
| $FeSO_4 \cdot 7H_2O$ | 0.4 |
| Distilled water to 1 liter | |
| pH adjusted to 7.0 before sterilization. | |

| Medium H | |
|---|---|
| | Grams |
| Yeast extract | 4 |
| Malt extract | 10 |
| Dextrose | 10 |
| Oatmeal | 10 |
| $FeSO_4 \cdot 7H_2O$ | 0.3 |
| Distilled water to 1 liter | |
| pH adjusted to 7.0 before sterilization. | |

| Medium I | |
|---|---|
| | Grams |
| Nutrisoy flour | 10 |
| Glucose | 10 |
| Oatmeal | 10 |
| $FeSO_4 \cdot 7H_2O$ | 0.3 |
| Distilled water to 1 liter | |
| pH adjusted to 7.0 before sterilization. | |

| Medium J | |
|---|---|
| | Grams |
| Nutrisoy flour | 10 |
| Glucose | 10 |
| Oatmeal | 20 |
| $(NH_4)_2SO_4$ | 0.3 |
| $FeSO_4 \cdot 7H_2O$ | 0.5 |
| $CaCO_3$ | 0.5 |
| Distilled water to 1 liter | |
| pH adjusted to 7.0 before sterilization. | |

EXAMPLE 11

Additional Micromonospora cultures tested for the production of β-lactamase inhibitor EM4615 give the following results:

| Culture | Activity v. RPI enzyme | |
|---|---|---|
| | Agar I | Agar II |
| Micromonospora chalcea ATCC 21561 | + | + |
| Micromonospora carbonacea ATCC 27114 | + | + |
| Micromonospora carbonacea ATCC 27115 | + | ± |

The cultures are grown by inoculating a yeast malt extract agar (Agar I) or beef extract agar (Agar II) and incubating for six days. After this time, the plates are overlaid with agar containing RP1 enzyme and reincubated at 37° for two hours. The plate is flood with a solution (500 μg/ml) of chromogenic cephalosporin. Production of the enzyme inhibitor is detected as yellow zones against a red background.

The agars have the following compositions:

| Agar I | | Agar II | |
|---|---|---|---|
| Yeast extract | 4 gm. | Beef extract | 3 gm. |
| Malt extract | 10 gm. | Tryptone | 5 gm. |
| Dextrose | 4 gm. | Yeast extract | 5 gm. |
| Distilled water to 1 liter | | Soluble starch | 24 gm. |
| The pH is adjusted to 7.3 with NaOH and 20 gms of agar are added. | | Dextrose | 1 gm. |
| | | Agar | 15 gm. |
| | | $CaCO_3$ | 4 gm. |
| | | Tap water | 1 liter |

What is claimed is:

1. A process for producing the β-lactamase inhibitor EM4615 which comprises cultivating a Micromonospora species capable of producing the β-lactamase inhibitor in an aqueous nutrient medium comprising an assimilable carbohydrate and an assimilable nitrogen source under submerged aerobic conditions until substantial β-lactamase inhibiting activity is imparted to the medium, and then recovering EM4615.

2. A process as in claim 1 wherein the solids are separated from the fermentation broth, the remaining broth is extracted with a lower alkanol and the alkanol extract is back extracted with water.

3. A process as in claim 1 wherein the Micromonospora species is *Micromonospora chalcea.*

4. A process as in claim 1 wherein the Micromonospora species is *Micromonospora carbonacea.*

5. A process as in claim 1 wherein the microorganism is cultivated at about 20° to 35° C. for about 48 to 240 hours.

6. A process for producing β-lactamase inhibitor EM4615 which comprises cultivating Micromonospora species capable of producing the β-lactamase inhibitor in an aqueous nutrient medium comprising an assimilable carbohydrate and an assimilable nitrogen source under submerged aerobic conditions for about 48 to 240 hours, separating the solids from the fermentation broth, extracting the remaining broth with a lower alkanol at about pH 2, and back extracting the alkanol extract at about pH 7 to 9.

7. A process as in claim 6 wherein the lower alkanol is n-butanol.

8. A process as in claim 6 wherein the Micromonospora species is *Micromonospora chalcea*.

9. A process as in claim 6 wherein the Micromonospora species is *Micromonospora carbonacea*.

10. β-lactamase inhibitor EM4615, and salts thereof, said EM4615 having an infrared spectrum, as the sodium salt, as in FIG. 1; having the following approximate elemental analysis as the sodium salt: C,49.99%; H,7.71%; O,23.69%; S,10.51%; Na,8.10%; the barium salt thereof melts in the range of about 144°–146° C., the sodium salt thereof is soluble in water and methanol and insoluble in acetone and chloroform; the barium salt thereof is soluble in dimethylsulfoxide and dimethylformamide and insoluble in water, methanol, acetone and chloroform.

* * * * *